(12) United States Patent
Lucio

(10) Patent No.: US 11,666,722 B2
(45) Date of Patent: Jun. 6, 2023

(54) NASAL CANNULA WITHOUT NOSTRIL PRONGS

(71) Applicant: 3B Medical, Inc., Winter Haven, FL (US)

(72) Inventor: Albert A. Lucio, Haines City, FL (US)

(73) Assignee: 3B Medical, Inc., Winter Haven, FL (US)

( * ) Notice: Subject to any disclaimer, the term of this patent is extended or adjusted under 35 U.S.C. 154(b) by 237 days.

(21) Appl. No.: 16/808,884

(22) Filed: Mar. 4, 2020

(65) Prior Publication Data

US 2021/0275769 A1    Sep. 9, 2021

(51) Int. Cl.
*A61M 16/06*    (2006.01)

(52) U.S. Cl.
CPC .  *A61M 16/0672* (2014.02); *A61M 2202/0208* (2013.01); *A61M 2209/088* (2013.01)

(58) Field of Classification Search
CPC .......... A61M 16/0672; A61M 16/0683; A61M 16/0666; A61M 16/0688
See application file for complete search history.

(56) References Cited

U.S. PATENT DOCUMENTS

| | | |
|---|---|---|
| 2,693,800 A | 11/1954 | Caldwell |
| 3,529,594 A | 9/1970 | Charnley et al. |
| 3,682,171 A | 8/1972 | Dali et al. |
| 4,216,769 A | 8/1980 | Grimes |
| 4,273,124 A | 6/1981 | Zimmerman |
| 5,526,806 A * | 6/1996 | Sansoni ............ A61M 16/0666 128/206.11 |
| 6,119,694 A * | 9/2000 | Correa ............. A61M 16/0666 128/207.13 |
| 7,007,694 B2 | 3/2006 | Aylsworth et al. |
| D549,323 S | 8/2007 | Kwok et al. |
| 7,383,839 B2 | 6/2008 | Porat et al. |
| D612,934 S | 3/2010 | Prentice et al. |
| D626,646 S | 11/2010 | Lubke et al. |
| D627,059 S | 11/2010 | Wood et al. |
| D662,200 S | 6/2012 | Eghbal |
| 8,684,005 B2 | 4/2014 | Jablons |
| D724,720 S | 3/2015 | O'Connior |
| 9,162,034 B2 | 10/2015 | Veliss et al. |

(Continued)

OTHER PUBLICATIONS

3B Medical Introduces Oxygen Nasal Cannula, rtmagazine.com, Posted Aug. 3, 2020.[online]. site visited May 3, 2022. URL:https://rtmagazine.com/products-treatment/monitoring-treatment/therapy-devices/3b-medical-freedom-x-nasal-cannula/ (Year 2020).

(Continued)

*Primary Examiner* — Joseph D. Boecker
*Assistant Examiner* — Thomas W Greig
(74) *Attorney, Agent, or Firm* — Carlson, Gaskey & Olds, P.C.

(57) ABSTRACT

This disclosure relates to a nasal cannula without nostril prongs. The nasal cannula may be used together with an oxygen delivery system, such as a portable oxygen concentrator, or another type of breathing device such as a continuous positive airway pressure (CPAP) machine. In an example, a nasal cannula includes a tube configured to connect to an oxygen supply, and further includes a fitting configured to connect to the tube. The fitting includes at least one discharge port and does not include nostril prongs.

20 Claims, 3 Drawing Sheets

(56) References Cited

U.S. PATENT DOCUMENTS

| | | | |
|---|---|---|---|
| 9,180,270 B2 | 11/2015 | Kapust et al. | |
| D745,141 S | 12/2015 | Hung | |
| D752,735 S | 3/2016 | Scampoli | |
| D757,930 S | 5/2016 | Baecke et al. | |
| 9,393,375 B2 | 7/2016 | Hernandez et al. | |
| D768,287 S | 10/2016 | Gusky | |
| 9,474,469 B2* | 10/2016 | Deutsch | A61B 5/085 |
| D825,053 S | 8/2018 | Ronayne et al. | |
| 10,166,357 B2* | 1/2019 | Veliss | A61M 16/0616 |
| D848,605 S | 5/2019 | Eury | |
| D849,242 S | 5/2019 | Wilson | |
| D849,243 S | 5/2019 | Wilson | |
| D859,646 S | 9/2019 | Scampoli | |
| D865,943 S | 11/2019 | Wilson et al. | |
| D878,549 S | 3/2020 | Wilson et al. | |
| D881,382 S | 4/2020 | Chang | |
| D893,013 S | 8/2020 | Higgins et al. | |
| D893,015 S | 8/2020 | Wilson | |
| D898,899 S | 10/2020 | Rummery | |
| 10,821,252 B2 | 11/2020 | Chodkowshi | |
| D911,515 S | 2/2021 | Koschany et al. | |
| D916,276 S | 4/2021 | Wilson et al. | |
| 10,987,480 B1 | 4/2021 | Lucio | |
| D933,206 S | 10/2021 | Lucio | |
| D983,015 S | 4/2023 | Jasmin et al. | |
| 2002/0092527 A1 | 7/2002 | Wood | |
| 2003/0079749 A1 | 5/2003 | Strickland | |
| 2003/0111081 A1 | 6/2003 | Gupta | |
| 2004/0226566 A1 | 11/2004 | Gunaratnam et al. | |
| 2005/0028822 A1 | 2/2005 | Sleeper et al. | |
| 2006/0107958 A1 | 5/2006 | Sleeper | |
| 2006/0266361 A1 | 11/2006 | Hernandez | |
| 2007/0107737 A1 | 5/2007 | Landis et al. | |
| 2010/0113956 A1 | 5/2010 | Curti | |
| 2010/0252042 A1* | 10/2010 | Kapust | A61M 16/0883 128/204.23 |
| 2010/0313898 A1 | 12/2010 | Richard et al. | |
| 2011/0073116 A1 | 3/2011 | Genger et al. | |
| 2011/0094518 A1* | 4/2011 | Cipollone | A61M 16/0683 128/207.18 |
| 2011/0214676 A1 | 9/2011 | Allum et al. | |
| 2012/0111332 A1* | 5/2012 | Gusky | A61M 16/0683 128/205.25 |
| 2012/0330183 A1 | 12/2012 | Allum | |
| 2014/0094669 A1* | 4/2014 | Jaffe | A61M 16/0858 128/207.18 |
| 2015/0068928 A1 | 3/2015 | Turner | |
| 2016/0051787 A1 | 2/2016 | Matsubara | |
| 2016/0095996 A1* | 4/2016 | Gusky | A61M 16/0816 128/205.25 |
| 2016/0271353 A1 | 9/2016 | Cheung | |
| 2017/0224942 A1 | 8/2017 | Barbour et al. | |
| 2019/0091428 A1 | 3/2019 | Chodkowski | |
| 2019/0099570 A1 | 4/2019 | Brambilla | |
| 2019/0240438 A1 | 8/2019 | Stenzler | |
| 2020/0023153 A1 | 1/2020 | Chou | |
| 2021/0275769 A1 | 9/2021 | Lucio | |
| 2021/0338960 A1 | 11/2021 | Schwaiger | |
| 2022/0047836 A1 | 2/2022 | Jagger | |
| 2022/0126052 A1 | 4/2022 | Fitch | |

OTHER PUBLICATIONS

3B Mask line up, 3B Medical, Youtube, [Posted on Mar. 26, 2019], [Site visited Aug. 20, 2021], Seen at URL: https://www.youtube.com/ watch?v=pf-rGz6o2WQ (Year: 2019).

Rio Replacement Nasal Pillow Cushion by 3B Medical,1800cpap.com,[Post date unknown], [Site visited Aug. 20, 2021], Seen at URL: https://www.1800cpap.com/rio-replacement-nasal-pillow-cushion-by-3b-medical?quantity=1&size=Large&gclid=EAlalQobChMl- 9LC4um_8glVi4rlCh0a%2525E2%252580%2525A6 (Year: 2021).

* cited by examiner

NASAL CANNULA WITHOUT NOSTRIL PRONGS

TECHNICAL FIELD

This disclosure relates to a nasal cannula without nostril prongs.

BACKGROUND

In the medical field, oxygen may be supplied to patients to treat a variety of conditions such as heart failure, chronic obstructive pulmonary disease (COPD), or any weakened lung or heart state. Portable oxygen concentrators (POCs) are one known device used in the medical field to supply supplemental oxygen to a patient. POCs take in ambient air, filter it, and deliver a relatively high purity flow of oxygen to the patient. At times, supplemental oxygen is used for purposes outside of the medical field, such as for recreational purposes. Supplemental oxygen may be used to shorten recovery time for exhausted athletes, or may be used at high altitudes to make breathing easier during skiing, mountain biking, or other sporting activities.

SUMMARY

A nasal cannula for an oxygen delivery system according to an exemplary aspect of the present disclosure includes, among other things, a tube configured to connect to an oxygen supply, and a fitting configured to connect to the tube. The fitting includes at least one discharge port and does not include nostril prongs.

In a further non-limiting embodiment of the foregoing nasal cannula, the at least one discharge port includes a first discharge port and a second discharge port, the first discharge port is configured to be situated inferior to a first nostril of a user, and the second discharge port is configured to be situated inferior to a second nostril of the user.

In a further non-limiting embodiments of any of the foregoing nasal cannulas, when the nasal cannula is worn by a user, the fitting is configured to be spaced-apart from a nose of the user.

In a further non-limiting embodiments of any of the foregoing nasal cannulas, the fitting includes a main body portion, and the first and second discharge ports are provided by openings in a superior surface of the main body portion.

In a further non-limiting embodiments of any of the foregoing nasal cannulas, the first and second discharge ports are spaced-apart from one another by a bridge section along a length of the main body portion.

In a further non-limiting embodiments of any of the foregoing nasal cannulas, the first and second discharge ports do not extend beyond the superior surface of the main body portion.

In a further non-limiting embodiments of any of the foregoing nasal cannulas, the superior surface of the main body portion is curved.

In a further non-limiting embodiments of any of the foregoing nasal cannulas, the superior surface of the main body portion is concave when viewed from above.

In a further non-limiting embodiments of any of the foregoing nasal cannulas, an inferior surface of the main body portion is convex when viewed from below.

In a further non-limiting embodiments of any of the foregoing nasal cannulas, a ratio between a length of the main body portion and a maximum height of the main body portion is about 2.2:1.

In a further non-limiting embodiments of any of the foregoing nasal cannulas, a distal surface of the main body portion is substantially convex when viewed from a position in front of the main body portion, and a proximal surface of the main body portion is substantially flat.

In a further non-limiting embodiments of any of the foregoing nasal cannulas, a ratio between a length of the main body portion to a distance between the distal surface and the proximal surface is about 2.2:1.

In a further non-limiting embodiments of any of the foregoing nasal cannulas, the main body portion includes a first prong projecting laterally from a first side of the main body portion, the first prong includes a first inlet port, the first inlet port is fluidly coupled to the first discharge port via a first internal passageway within the first prong and the main body portion, the main body portion includes a second prong projecting laterally from a second side of the main body portion, the second prong includes a second inlet port, and the second inlet port is fluidly coupled to the second discharge port via a second internal passageway within the second prong and the main body portion.

In a further non-limiting embodiments of any of the foregoing nasal cannulas, a first portion of the tube is configured to fit over the first prong, and a second portion of the tube is configured to fit over the second prong.

In a further non-limiting embodiments of any of the foregoing nasal cannulas, the first internal passageway includes a straight section within the first prong and a curved section within the main body portion between the straight section and the first discharge port, and the second internal passageway includes a straight section within the second prong and a curved section within the main body portion between the straight section and the second discharge port.

In a further non-limiting embodiments of any of the foregoing nasal cannulas, the fitting is integrally formed as a one-piece structure.

In a further non-limiting embodiments of any of the foregoing nasal cannulas, the fitting is provided by an integrally molded piece of plastic A system according to an exemplary aspect of the present disclosure includes, among other things, a nasal cannula including a tube and a fitting connected to the tube. The fitting includes at least one discharge port and does not include nostril prongs. Further, an oxygen supply connected to the tube and including a blower and a sensor. The blower is configured to deliver oxygen to the tube when information from the sensor indicates a change in pressure corresponding to either an inhale or exhale of a patient.

In a further non-limiting embodiments of the foregoing systems, the blower is configured to deliver oxygen to the tube when information from the sensor indicates a change in pressure as low as 0.05 cm $H_2O$.

In a further non-limiting embodiments of any of the foregoing systems, the blower is configured to deliver oxygen to the tube when information from the sensor indicates a change in pressure within a range of as 0.05 cm $H_2O$ and 0.3 cm $H_2O$.

DETAILED DESCRIPTION

This disclosure relates to a nasal cannula without nostril prongs. The nasal cannula may be used together with an oxygen delivery system, such as a portable oxygen concentrator, or another type of breathing device such as a continuous positive airway pressure (CPAP) machine. In an example, a nasal cannula includes a tube configured to connect to an oxygen supply, and further includes a fitting configured to connect to the tube. The fitting includes at least one discharge port and does not include nostril prongs. Because the fitting does not include nostril prongs, patient comfort is dramatically increased relative to prior designs. These and other benefits will be appreciated from the below description.

Figure 1:
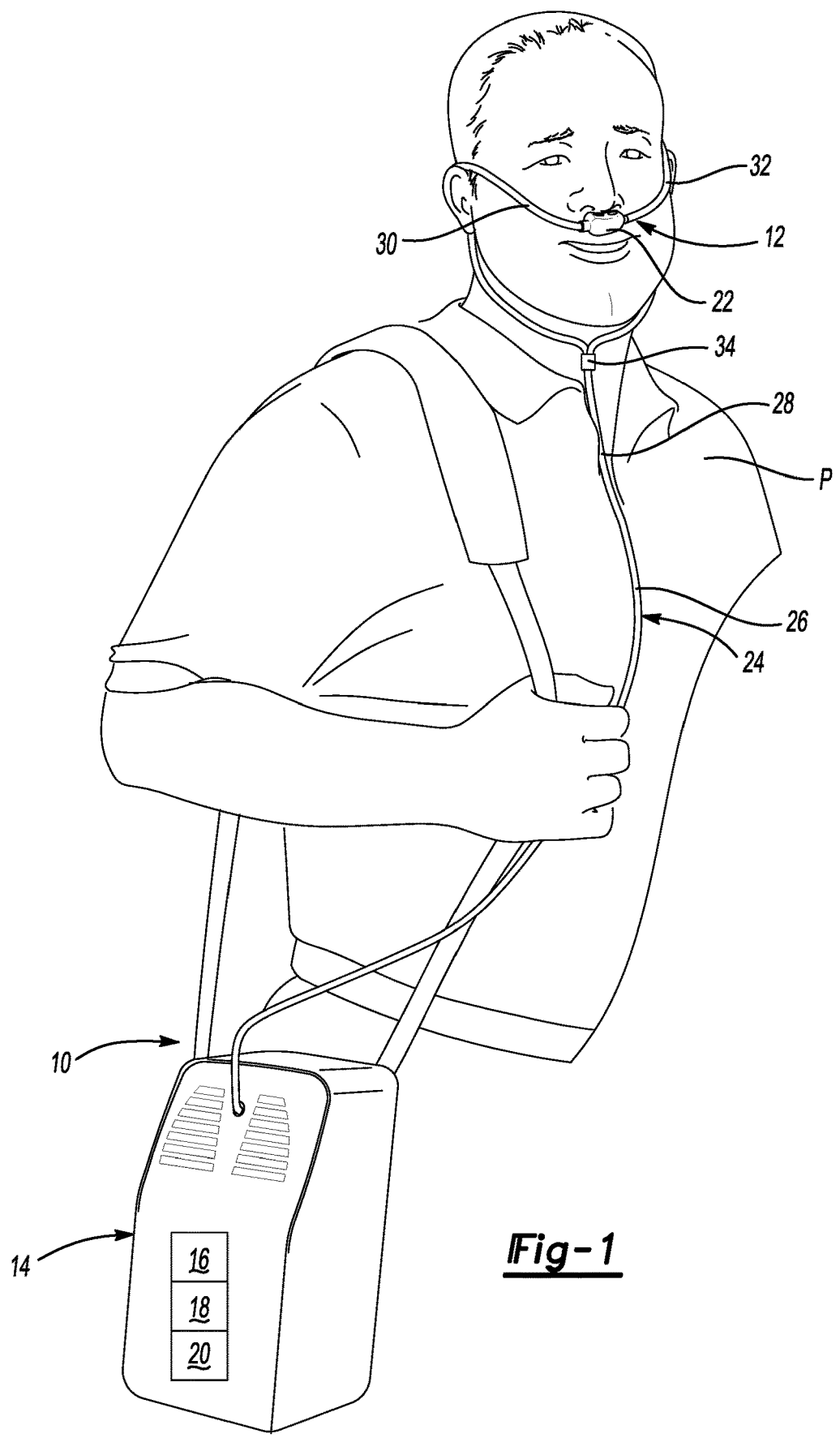
FIG. 1 illustrates, somewhat schematically, an example oxygen delivery system.

FIG. 1 illustrates an example oxygen delivery system 10 ("system 10") with a cannula 12 and an oxygen supply 14. The cannula 12 may be considered a cannula assembly, as it may contain more than one piece, such as a tube and a nasal fitting, among other pieces (such as connectors and collars) as explained below. The oxygen supply 14 is configured to deliver a flow of supplemental oxygen or increased airflow to a patient, or person, P, who is typically a person in need of respiratory help. Alternatively, the patient P could be a person who does not require oxygen for medical purposes but, on the contrary, is an athlete using oxygen for recovery purposes. Further, the patient P could be an athlete engaging in extreme sports, such as skiing or mountain biking, and in particular the patient P could be engaging in such sports at substantially high altitudes, such as in mountainous regions.

In FIG. 1, the oxygen supply 14 is a portable oxygen concentrator (POC). It should be understood that this disclosure extends to cannulas used with other types of oxygen supplies, including oxygen tanks, stationary oxygen concentrators, or a wall connection in a hospital via a flowmeter. This disclosure also extends to cannulas used with other breathing aids, such as a continuous positive airway pressure (CPAP) machine.

The oxygen supply 14 includes an blower 16, such as a pump and/or an air compressor, a sensor 18, and a controller 20, among other structures, such as one or more filters, such as a molecular sieve which separates (i.e., adsorbs) nitrogen from ambient air, and a battery. The blower 16, sensor 18, and controller 20 are shown schematically in FIG. 1. The oxygen supply 14 may use pressure swing adsorption (PSA), vacuum swing adsorption (VSA), or pressure vacuum swing adsorption (PVSA) technology. The oxygen supply 14 may further include a storage chamber, or reservoir. The battery of the oxygen supply 14 may be rechargeable.

Figure 2:
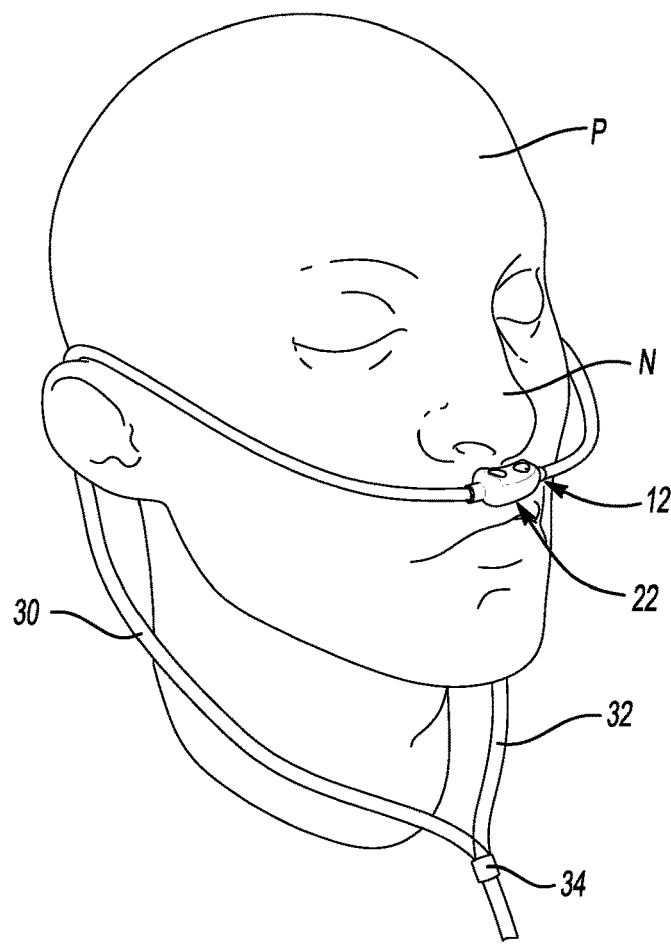
FIG. 2 is a close-up view of a portion of an example cannula relative to a head and neck of a patient.

The oxygen supply 14 delivers oxygen via the cannula 12 to an interface, which in this example is provided by a nasal fitting 22 ("fitting 22"). The fitting 22 rests beneath a nose of the patient P and delivers oxygen to patient P via their nose N (FIG. 2). The oxygen supply 14 may be a pulse delivery device or a continuous flow device. A continuous flow POC provides a continuous flow of oxygen to the patient. A pulse delivery POC only provides oxygen when the patient P is inhaling. The sensor 18 is configured to generate information (i.e., a signal) indicative of when the patient P is inhaling by detecting a change in pressure. In this sense, the sensor 18 may be considered a pressure sensor. The controller 20 is configured to interpret the signal from the sensor 18 and, when a particular change in pressure is identified, the controller 20 instructs the blower 16 to deliver a pulse of oxygen to the person P. As will be discussed below, the sensor 18 is relatively sensitive compared to traditional sensors, and the controller 20 is configured to instruct the blower 16 to provide a pulse of oxygen when a relatively low change in pressure is met or exceeded.

Ambient air contains about 21% oxygen and about 79% nitrogen and other gases. The oxygen supply 14 compresses the ambient air and filters the nitrogen out of the air, leaving oxygen as the primary gas in the product delivered to the user via the fitting 22. The nitrogen is released back to the ambient environment and/or held in the filters. In a typical medical grade POC, the gas delivered to the patient P is around 90-95% oxygen. In other embodiments, such as in POCs for recreational use, a lower oxygen purity is delivered to the patient P. The oxygen supply 14 may include flow control buttons and indicators for breath detection or alerts, and sometimes includes the ability to toggle between a continuous flow and a pulse flow.

The controller 20 may include hardware and/or software, and may be programmed with executable instructions for interfacing with and operating the various components of the oxygen supply 14. In an embodiment, the controller 20 and the sensor 18 are mounted to a common printed circuit board within the oxygen supply 14. It should be understood that the controller 20 could be part of an overall control module. The controller 20 includes a processing unit and non-transitory memory for executing the various control strategies and modes of the oxygen system 14.

In this example, the cannula 12 includes a tube 24 fluidly connecting the oxygen supply 14 to the fitting 22. The tube 24, in this example, includes a main section 26 connected directly to the oxygen supply 14 and extending to a split 28. At the split 28, the tube 24 branches into a first portion 30 and a second portion 32, each of which are connected directly to a respective side of the fitting 22. The first and second portions 30, 32 wrap around opposite ears of the patient P. An adjustable collar 34, which is slidable along the first and second portions 30, 32, is below a chin of the patient P.

The fitting 22 rests below a nose N of the patient, as shown in FIG. 2. In particular, the fitting 22 rests against the face of the patient P, specifically against the philtrum, including the philtral dimple and/or the philtral columns, at a location superior to (e.g., vertically above) the upper lip and inferior to (e.g., vertically below) the base of the nose N.

The fitting 22 does not include nostril prongs, which are found in traditional nasal cannulas and CPAP nasal pillows. Nostril prongs are structures, namely protrusions, which enter into the nostrils of the patient P. In this disclosure, the fitting 22 does not include any such structures that project into the nostrils of the patient P. In fact, in some examples, the fitting 22 is spaced-apart from the nose N of the patient P, and rests against an area superior to the upper lip of the patient P without directly contacting the nose N. In other examples, the columella (i.e., the inferior margin of the septum), of the nose N may contact a superior (i.e., upper) surface of the fitting 22. In either example, no portion of the fitting 22 enters the nostrils of the patient P. Further, in this disclosure, the fitting 22 does not surround the tip of the nose, as is common in some known CPAP masks and CPAP pillows.

Figure 3:
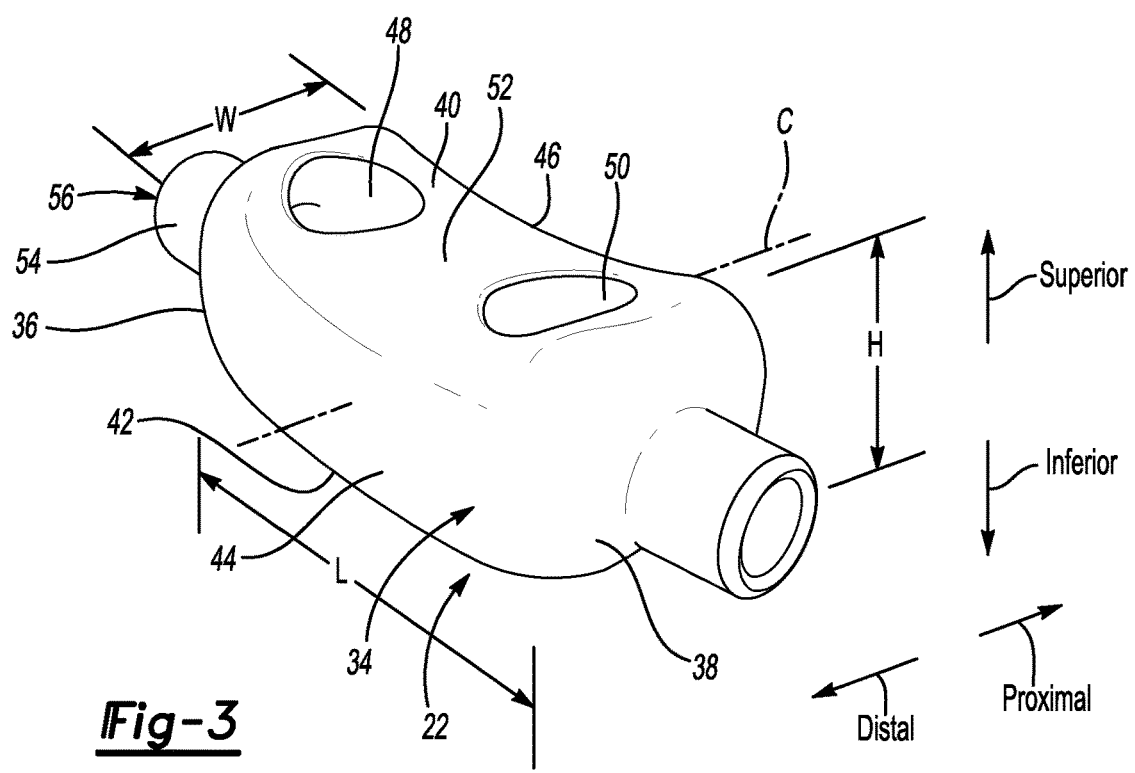
FIG. 3 is a front-perspective view of an example fitting of the example cannula.
Figure 4:
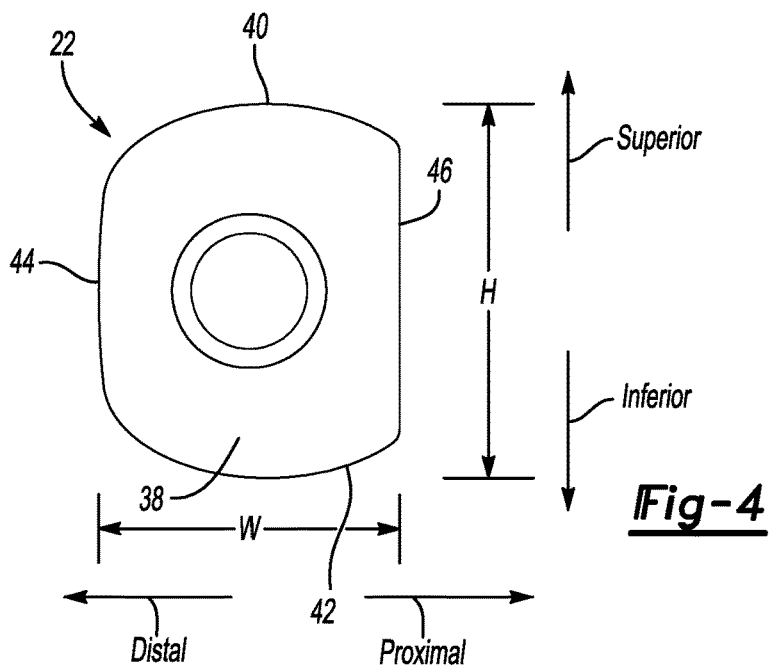
FIG. 4 is a side of view of the example fitting.

FIGS. 3 and 4 illustrate additional detail of the fitting 22. The fitting 22 includes a main body portion 34 which is substantially symmetrical about a centerline C. The main body portion 34 includes a length L extending between a first lateral side 36 and a second lateral side 38 of the main body portion 34. In an example, the length L is 22 mm. The term lateral refers to the lateral direction, which is substantially normal to the centerline C.

The main body portion 34 also includes a height H vertically between a superior (i.e., vertically upper) surface 40 and an inferior (i.e., vertically lower) surface 42. In one example, a ratio between a length L and the height H is about 2.2:1. The height H is 10 mm in an example. The main body portion 34 further includes a width W extending in a direction parallel to the centerline C between a distal (i.e., forward facing) surface 44 and a proximal (i.e., rearward facing) surface 46. A ratio between a length L and the width W is 2.2:1 The width W is 10 mm in an example. The ratio between the width W and height H is 1:1 in an example.

Figure 5:
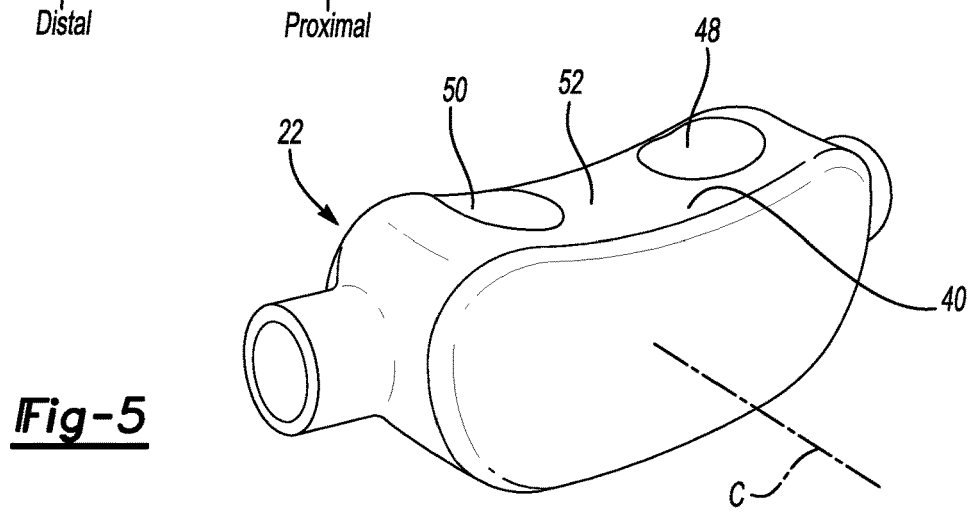
FIG. 5 is a rear-perspective view of the example fitting.

The superior surface 40 includes at least one discharge port configured to deliver fluid to the nose N of the patient P. In this example, the superior surface 40 includes a first discharge port 48 and a second discharge port 50. The first and second discharge ports 48, 50 are spaced-apart from one another along length L of the main body portion 34, which is in a direction normal to the centerline C, by a bridge section 52 (FIG. 5) of the superior surface 40. The first and second discharge ports 48, 50 are openings that are circular in shape in this example, and are arranged on opposite lateral sides of the bridge section 52. The first and second discharge ports 48, 50 do not project from or extend beyond, in the superior direction, to the superior surface 40.

When worn by the patient, the first discharge port 48 is configured to be situated inferior to (i.e., vertically beneath) a right nostril (from the patient's perspective) of the patient P and the second discharge port 50 is configured to be situated inferior to a left nostril of the patient P. Further, the bridge section 52 is configured to be situated inferior to a septum of the nose N of the patient P. In some examples, the bridge section 52 may directly contact a septum of the nose N of the patient P, while in some other examples the bridge section 52 is spaced-apart from a septum of the nose N of the patient.

In an aspect of this disclosure, the fitting 22 exhibits a contour that facilitates ease of use by patients. In particular, as perhaps best seen in FIG. 5, the superior surface 40 is curved in one example such that the superior surface 40 is concave when viewed from above (i.e., from a superior location). The bridge section 52 is a bottom-most portion of the superior surface 40. The discharge ports 48, 50 are at a superior location relative to the bridge section 52, and the laterally-outer edges of the superior surface 40 are superior to the discharge ports 48, 50. Such curvature permits a comfortable fit beneath the nose N while maintaining proper position of the discharge ports 48, 50 for fluid delivery.

The inferior surface 42 is curved in this example such that it is convex when viewed from below (i.e., from an inferior location). Such a curvature prevents interference with an upper lip of the patient P. Further, the distal surface 44 is substantially convex when viewed from a position in front of (i.e., distal to) the main body portion 34, and the proximal surface 46 is substantially flat. The proximal surface 46 may lie in a plane running perpendicular to the centerline C. Alternatively, the proximal surface 46 may be curved. The curvature of the distal surface 44 prevents interference and provides a relatively smooth forward-facing surface, whereas the flat proximal surface 46 facilitates connection to the face of the patient.

Figure 6:
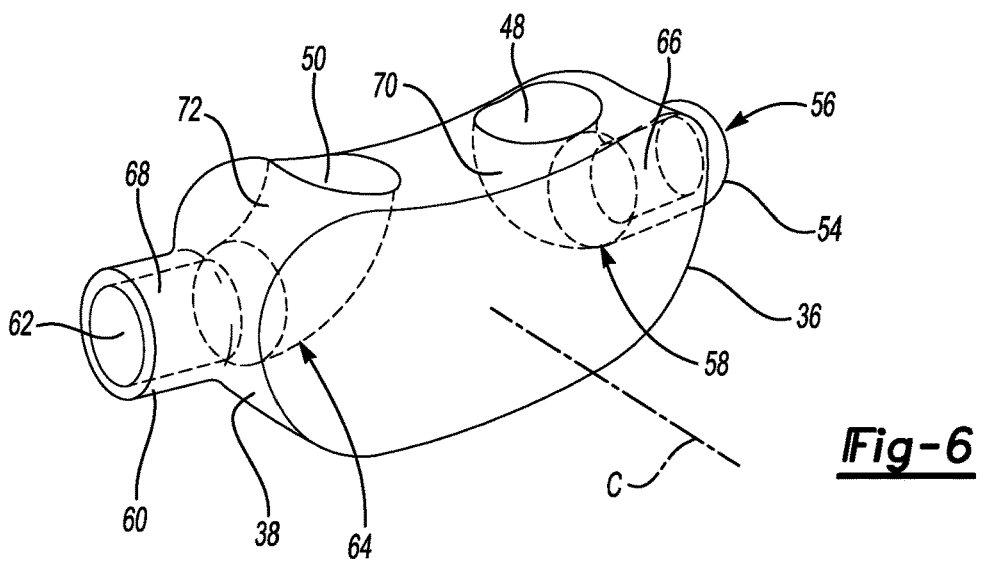
FIG. 6 is also a rear-perspective view of the example fitting and illustrates internal passageways within the fitting in phantom.

The fitting 22 includes at least one prong configured to interface with a portion of the tube 24 and, in particular, to fluidly couple the fitting 22 to the tube 24. In this example, the fitting 22 includes a first prong 54 projecting laterally from a first side 36 of the main body portion 34, and the first prong 54 includes a first inlet port 56. The first inlet port 56 is fluidly coupled to the first discharge port 48 via a first internal passageway 58 (FIG. 6) which is within the first prong 54 and the main body portion 34. Likewise, the main body portion 34 includes a second prong 60 projecting laterally from the second side 38, and the second prong 60 includes a second inlet port 62. The second inlet port 62 is fluidly coupled to the second discharge port 50 via a second internal passageway 64 within the second prong 60 and the main body portion 34.

In this example, an end of the first portion 30 of the tube 24 is configured to fit over the first prong 54, and an end of the second portion 32 of the tube 24 is configured to fit over the second prong 60. The first and second prongs 54, 60 may include ribs or flanges configured to interface with the respective ends of the first and second portions 30, 32.

In this disclosure, the first and second internal passageways 58, 64 include straight sections 66, 68 within a respective one of the first and second prongs 54, 60. The straight sections 66, 68 extend substantially normal to the centerline C and are concentric with the respective first and second prong 54, 60. The first and second the first internal passageways 58, 64 also include a curved section 70, 72 within the main body portion 34 between a respective straight section 66, 68 and a corresponding first or second discharge port 48, 50. In this example, the curved sections 70, 72 cause fluid within the first and second internal passageway 58, 64 to make substantially a 90-degree turn from flowing in a direction lateral normal to, and toward, the centerline C to flowing in a direction normal to, and away from, the centerline C, specifically in the superior direction toward the nose N of the patient P.

The fitting 22 is integrally formed as a one-piece structure in one example. In particular, the fitting 22 is provided by an integrally molded piece of plastic. In some embodiments, the fitting 22 is made entirely of silicone, or another soft elastomer. The fitting 22 may be made of same material as tube 24 or a different material. While above the fitting 22 was described as being separate from the tube 24, the fitting 22 could be formed integrally with the tube 24.

Because the fitting 22 does not include nostril prongs and no portion of the fitting 22 enters the nostrils of the patient P, patient comfort is dramatically increased relative to traditional nasal cannula and nasal pillow designs. However, because the discharge ports of the fitting 22 are further away from the nostrils of the patient P than in cannulas with nostril prongs, for example, various operating parameters and settings of the oxygen supply 14 are adjusted in this disclosure. In particular, in an aspect of this disclosure, the sensitivity of the sensor 18 is increased. In particular, the controller 20 is configured to identify, based on the information (e.g., signal) from the sensor 18, an exhale or inhale of the patient P at a lower change in pressure than in traditional nasal cannulas. In an example, the controller 20 instructs the blower 16 to deliver a flow of fluid (e.g., oxygen) when the sensor 18 indicates a change in pressure as low as 0.05 cm $H_2O$. In a further example, the controller 20 instructs the blower 16 to deliver a flow of fluid (e.g., oxygen) when the sensor 18 indicates a change in pressure within a range of as 0.05 cm $H_2O$ and 0.3 cm $H_2O$. Further, to account for potential losses due to the space between the fitting 22 and the nose N, the blower 16 could deliver fluid at a higher rate than in systems with traditional nasal cannulas.

It should be understood that terms such as "generally," "substantially," and "about" are not intended to be boundaryless terms, and should be interpreted consistent with the way one skilled in the art would interpret those terms. Further, various directional terms, such as "superior," "inferior," "distal," "proximal," etc., have been used herein and labeled in some figures for ease of reference. These directional terms are used with reference to the normal operational Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A nasal cannula for an oxygen delivery system, comprising:
   a tube configured to connect to an oxygen supply; and
   a fitting configured to connect to the tube and configured to rest below a nose of a patient, wherein the fitting includes a main body including a proximal surface configured to rest against an area superior to an upper lip of the patient, and a superior surface including a first discharge port and a second discharge port spaced apart by a bridge section;
   wherein the first and second discharge ports are configured to be situated inferior to and aligned with, respectively, a first and a second nostril of the patient;
   wherein the bridge section includes an inferior-most portion of the superior surface and laterally-outermost edges of the superior surface are at a superior location relative to the inferior-most portion;
   wherein the main body portion includes a first prong projecting laterally from a first side of the main body portion and a second prong projecting laterally from a second side of the main body portion, the first and second prongs including, respectively, a first inlet port and a second inlet port;
   wherein the first inlet port is fluidly coupled to the first discharge port via a first internal passageway within the first prong and the main body portion, and the second inlet port is fluidly coupled to the second discharge port via a second internal passageway within the first second prong and the main body portion;
   wherein the first and second internal passageways are separate, discrete passageways configured such that fluid within one of the first and second internal passageways does not intermix with fluid in the other of the first and second internal passageways; and
   wherein the fitting does not include nostril prongs, and no portion of the fitting is configured to project from the superior surface towards the nose of the patient.

2. The nasal cannula as recited in claim 1, wherein, when the nasal cannula is worn by the patient, the fitting is configured to be spaced-apart from the nose of the patient.

3. The nasal cannula as recited in claim 1, wherein an inferior surface of the main body portion is convex when viewed from below.

4. The nasal cannula as recited in claim 3, wherein a ratio between a length of the main body portion and a maximum height of the main body portion is about 2.2:1.

5. The nasal cannula as recited in claim 1, wherein:
   a distal surface of the main body portion is substantially convex when viewed from a position in front of the main body portion, and
   the proximal surface of the main body portion is substantially flat.

6. The nasal cannula as recited in claim 5, wherein a ratio between a length of the main body portion to a distance between the distal surface and the proximal surface is about 2.2:1.

7. The nasal cannula as recited in claim 1, wherein:
   a first portion of the tube is configured to fit over the first prong, and
   a second portion of the tube is configured to fit over the second prong.

8. The nasal cannula as recited in claim 1, wherein:
   the first internal passageway includes a straight section within the first prong and a curved section within the main body portion between the straight section and the first discharge port, and
   the second internal passageway includes a straight section within the second prong and a curved section within the main body portion between the straight section and the second discharge port.

9. The nasal cannula as recited in claim 1, wherein the fitting is integrally formed as a one-piece structure.

10. The nasal cannula as recited in claim 9, wherein the fitting is provided by an integrally molded piece of plastic.

11. The nasal cannula as recited in claim 1, wherein the fitting further includes a distal surface opposite the proximal surface, the superior surface configured to extend distally from the patient from the proximal surface to the distal surface.

12. The nasal cannula as recited in claim 11, wherein the proximal surface is configured to face in a proximal direction towards the patient and the distal surface faces in a distal direction opposite the proximal direction.

13. The nasal cannula as recited in claim 1, wherein the superior surface is configured to face in a superior direction and the proximal surfaces is configured to face in a proximal direction towards the patient, the proximal direction normal to the superior direction.

14. The nasal cannula as recited in claim 1, wherein, when the nasal cannula is worn by the patient, the superior surface is configured to contact the nose of the patient.

15. The nasal cannula as recited in claim 1, wherein the first and second discharge ports each include an opening that is at a superior location relative to the inferior-most portion.

16. The nasal cannula as recited in claim 1, wherein the first internal passageway is symmetrical with the second internal passageway about a centerline of the main body portion.

17. A system, comprising:
   a nasal cannula including a tube and a fitting connected to the tube an oxygen supply connected to the tube and including a blower and a sensor, wherein the blower is configured to deliver oxygen to the tube when information from the sensor indicates a change in pressure corresponding to either an inhale or exhale of a patient, wherein the blower is configured to deliver oxygen to the tube when information from the sensor indicates a change in pressure as low as 0.05 cm H₂O;

wherein the fitting is configured to rest below a nose of the patient and includes a main body including a proximal surface configured to rest against an area superior to an upper lip of the patient, and a superior surface including a first discharge port and a second discharge port spaced apart by a bridge section;

wherein the first and second discharge ports are configured to be situated inferior to and aligned with, respectively, a first and a second nostril of the patient;

wherein the bridge section includes an inferior-most portion of the superior surface and laterally-outermost edges of the superior surface are at a superior location relative to the inferior-most portion;

wherein the main body portion includes a first prong projecting laterally from a first side of the main body portion and a second prong projecting laterally from a second side of the main body portion, the first and second prongs including, respectively, a first inlet port and a second inlet port;

wherein the first inlet port is fluidly coupled to the first discharge port via a first internal passageway within the first prong and the main body portion, and the second inlet port is fluidly coupled to the second discharge port via a second internal passageway within the first second prong and the main body portion;

wherein the fitting does not include nostril prongs, an no portion of the fitting is configured to project from the superior surface towards the nose of the patient; and wherein the fitting is formed as a one-piece structure and provided by an integrally molded piece of plastic.

18. The system as recited in claim 17, wherein the blower is configured to deliver oxygen to the tube when information from the sensor indicates a change in pressure within a range of 0.05 cm H₂O and 0.3 cm H₂O.

19. A nasal fitting, comprising:

a main body including a proximal surface configured to rest against an area superior to an upper lip of a patient, and a superior surface including a first discharge port and a second discharge port spaced apart by a bridge section;

wherein the first and second discharge ports are configured to be situated inferior to and aligned with, respectively, a first and a second nostril of the patient;

wherein the superior surface is concave when viewed from above such that the bridge section includes an inferior-most portion of the superior surface and the first and second discharge ports each include an opening that is at a superior location relative to the inferior-most portion;

wherein the nasal fitting does not include nostril prongs, and no portion of the fitting is configured to project from the superior surface towards the nose of the patient; and wherein the nasal fitting is formed as a one-piece structure and provided by an integrally molded piece of plastic.

20. The nasal fitting as recited in claim 19, wherein:

the main body portion includes a first prong projecting laterally from a first side of the main body portion and a second prong projecting laterally from a second side of the main body portion, the first and second prongs including, respectively, a first inlet port and a second inlet port;

the first inlet port is fluidly coupled to the first discharge port via a first internal passageway within the first prong and the main body portion, and the second inlet port is fluidly coupled to the second discharge port via a second internal passageway within the second prong and the main body portion; and the first and second internal passageways are separate, discrete passageways configured such that fluid within one of the first and second internal passageways does not intermix with fluid in the other of the first and second internal passageways.

* * * * *